(12) United States Patent
Carlsson et al.

(10) Patent No.: US 11,285,173 B2
(45) Date of Patent: *Mar. 29, 2022

(54) DIALYSIS SOLUTION, FORMULATED AND STORED IN TWO PARTS, COMPRISING PHOSPHATE

(71) Applicant: GAMBRO LUNDIA AB, Lund (SE)

(72) Inventors: Ola Carlsson, Lund (SE); Malin Ernebrant, Blentarp (SE); Gunita Forsback, Loddekopinge (SE); Anders Wieslander, Lund (SE); Therese Svensson, Genarp (SE)

(73) Assignee: Gambro Lundia AB, Lund (SE)

( * ) Notice: Subject to any disclaimer, the term of this patent is extended or adjusted under 35 U.S.C. 154(b) by 0 days.

This patent is subject to a terminal disclaimer.

(21) Appl. No.: 16/941,992

(22) Filed: Jul. 29, 2020

(65) Prior Publication Data

US 2020/0384019 A1    Dec. 10, 2020

Related U.S. Application Data (60) Continuation of application No. 15/057,219, filed on Mar. 1, 2016, now Pat. No. 10,729,722, which is a division of application No. 11/658,001, filed as application No. PCT/SE2005/001550 on Oct. 14, 2005, now Pat. No. 10,729,721.

(60) Provisional application No. 60/522,624, filed on Oct. 21, 2004.

(30) Foreign Application Priority Data

Oct. 14, 2004 (SE) .................................... 0402507-8

(51) Int. Cl.
| | |
|---|---|
| A61K 33/42 | (2006.01) |
| A61K 9/08 | (2006.01) |
| A61K 33/10 | (2006.01) |
| A61K 31/7004 | (2006.01) |
| A61K 33/00 | (2006.01) |
| A61K 33/14 | (2006.01) |
| A61K 9/00 | (2006.01) |
| A61J 1/10 | (2006.01) |
| A61M 1/16 | (2006.01) |
| A61M 1/28 | (2006.01) |

(52) U.S. Cl.
CPC .............. *A61K 33/42* (2013.01); *A61J 1/10* (2013.01); *A61K 9/0019* (2013.01); *A61K 9/08* (2013.01); *A61K 31/7004* (2013.01); *A61K 33/00* (2013.01); *A61K 33/10* (2013.01); *A61K 33/14* (2013.01); *A61M 1/1654* (2013.01); *A61M 1/287* (2013.01)

(58) Field of Classification Search
None
See application file for complete search history.

(56) References Cited

U.S. PATENT DOCUMENTS

| | | | |
|---|---|---|---|
| 3,970,750 | A | 7/1976 | Brockemeyer et al. |
| 3,993,750 | A | 11/1976 | Fox, Jr. |
| 4,548,817 | A | 10/1985 | Filley et al. |
| 4,630,727 | A | 12/1986 | Feriani et al. |
| 4,663,166 | A | 5/1987 | Veech |
| 5,211,643 | A | 5/1993 | Reinhardt |
| 5,261,872 | A | 11/1993 | Goldenberg |
| 5,296,242 | A | 3/1994 | Zander |
| 6,017,942 | A | 1/2000 | Bergstrom |
| 6,156,007 | A | 12/2000 | Ash |
| 6,232,128 | B1 | 5/2001 | Iguchi et al. |
| 6,277,815 | B1 | 8/2001 | Knerr |
| 6,309,673 | B1 | 10/2001 | Duponchelle et al. |
| 6,348,162 | B1 | 2/2002 | Ash |
| 6,689,393 | B1 | 2/2004 | Knerr |
| 6,743,191 | B1 | 6/2004 | Chang |
| 2003/0138501 | A1 | 7/2003 | Elisabettini |
| 2007/0298125 | A1 | 12/2007 | Ernebrant et al. |
| 2008/0085325 | A1 | 4/2008 | Carlsson et al. |

FOREIGN PATENT DOCUMENTS

| | | |
|---|---|---|
| CN | 1222069 A | 7/1999 |
| CN | 1336825 | 2/2002 |
| CN | 1427716 | 7/2003 |
| EP | 0437274 | 7/1991 |
| EP | 0437274 | 5/1994 |
| EP | 0776649 | 6/1997 |
| EP | 0643969 B1 | 12/1998 |
| EP | 0185759 B2 | 6/2004 |
| JP | 57091912 | 8/1982 |
| JP | 2000-016484 | 1/2000 |
| WO | WO 83/00293 | 2/1983 |
| WO | WO 86/00227 | 1/1986 |
| WO | WO 91/10457 | 7/1991 |
| WO | WO 98/29434 | 7/1998 |
| WO | WO 01/00204 A1 | 1/2001 |

(Continued)

OTHER PUBLICATIONS

Decision to Refuse a European Patent Application for Application No. 05793316.0-1460 dated May 13, 2016 (17 pages).
APIC Position Paper: Safe Injection, Infusion, and Medication Vial Practices in Health Care (2016), 18 pages.
Dunham et al., "The Solubility of Calcium and Phosphorus in Neonatal Total Parenteral Nutrition Solutions", *J. of Parenteral and Enteral Nutrition*, vol. 15, No. 6, 1991, pp. 608-611.
Goldmann, et al., Guidelines for Infection Control, *Annals of Internal Medicine*, vol. 79, No. 6, Dec. 1973, 4 pages.
Gudeman et al., "Potential Risks of Pharmacy Compounding", *Drugs R D*, vol. 13, 2013, pp. 1-8.
Ing et al., "Preparation of Phosphate-Containing Dialysate for Use in Hemodialysis and Peritoneal Dialysis", *The Int. J. of Artificial Organs*, vol. 6, No. 6, 1983, pp. 321-322.

(Continued)

*Primary Examiner* — Jessica Worsham
(74) *Attorney, Agent, or Firm* — Mueting Raasch Group (57) ABSTRACT

The present invention relates to a medical solution. According to the invention the ready-for-use solution comprises phosphate in a concentration of 1.0-2.8 mM, is sterile and has a pH of 6.5-7.6. The present invention further relates to a method for producing the medical solution and the use thereof.

10 Claims, 3 Drawing Sheets

(56) References Cited

FOREIGN PATENT DOCUMENTS

| WO | WO 01/89478 | 11/2001 |
|---|---|---|
| WO | WO 03/075982 | 9/2003 |
| WO | WO 2005/082383 | 9/2005 |

OTHER PUBLICATIONS

Monograph "Liquid Preparations for Oral Use" of the European Pharmacopoeia 7.0. Jan. 2008.
Monograph "Liquid Preparations for Oral Use" of the European Pharmacopoeia 4.0. Jan. 2002.
Monograph "Methods of Preparation of Sterile Products" of the European Pharmacopoeia 7.0. Jan. 2008.
Monograph "Methods of Preparation of Sterile Products" of the European Pharmacopoeia 4.0.
Monograph "Parenteral Preparations" of the European Pharmacopoeia 4.0. Jan. 2002.
Monograph "Parenteral Preparations" of the European Pharmacopoeia 7.0. Jan. 2008.
Monograph "Particulate Contamination: Sub-Visible Particles" of the European Pharmacopoeia 8.0. Apr. 2011.
Monograph "Particulate Contamination: Sub-Visible Particles" of the European Pharmacopoeia 4.0.
Monograph "Uniformity of Content of Single-Dose Preparations" of the European Pharmacopoeia 4.0.
Monographs on Hemodialysis Solutions and Hemofiltration/Hemodiafiltration Solutions of the European Pharmacopoeia 4.0. Jan. 2002.
Paul, John, "Cell and Tissue Culture" Fifth Edition, Chapter VI (1975), 36 pgs.
Product Information of Fleet Phospho-Soda. Apr. 30, 2010.
Product Information of Hemosol B0. May 5, 2006.
Recommendations for Infection Control for the Practice of Anesthesiology (Third Edition, 86 pages.
USP 38 Chapter 797, Physical Tests, Pharmaceutical Compounding—Sterile Preparations, pp. 567-579.
Yessayan et al., "Continuous Renal Replacement Therapy for the Management of Acid-Base and Electrolyte Imbalances in Acute Kidney Injury", *Advances in Chronic Kidney Disease,* vol. 23, No. 3, May 2016, pp. 203-210.
Bach et al., "The Use of Tissue Slices for Pharmacotoxicology Studies," ATLA (1996), vol. 24, pp. 893-923.
Bambauer, R et al., "Bacteria- and Endotoxin-Free Dialysis Fluid for Use in Chronic Hemodialysis," Artificial Organs, vol. 18. No. 3, pp. 188-192, Mar. 1994.
Birrer et al., Handbook of Modem Pharmaceutical Analysis (2001), Chapter 7, Parenteral Dosage Forms, pp. 269-305.
European Pharmacopeia, Supplement to vol. III, 1977, Paris, France, Title page and table of contents. 3 pages.
Ing et al., "Increasing Plasma Phosphorus Values by Enriching with Phosphorus the "Acid Concentrate" of a Bicarbonate-Buffered Dialysate Delivery System," The International Journal of Artificial Organs, vol. 15, No. 12, 1992, pp. 701-703.
International Search Report of International Application No. PCT/US85/01202 (dated 1985).
Leehey et al., "Correction of Hypercalcemia and Hypophosphatemia by Hemodialysis Using a Conventional, Calcium-Containing Dialysis Solution Enriched with Phosphorus," American Journal of Kidney Diseases, vol. 29, No. 2, Feb. 1997, pp. 288-290.
Phelan, "Basic Techniques for Mammalian Cell Tissue Culture," Current Protocols in Cell Biology (1998), pp. 1-10.
Physicians' Desk Reference, 28th Ed. (1974), p. 1257.
Troyanov, "Phosphate Addition to Hemodiafiltration Solutions During Continuous Renal Replacement Therapy", Intensive Care Medicine, Aug. 2004, LNKD-PUBMED: 15156308, vol. 30, No. 8, Aug. 2004, pp. 1662-1665, XP002677818, ISSN:0342-4642.
Yu, "Raising Plasma Phosphorus Levels by Phosphoms-Enriched Bicarbonate-Containing Dialysate in Hemodialysis Patients", Artificial Organs, vol. 16, No. 4, 1992, pp. 414-416, XP002677817, ISSN:0160-564X.
Zabaneh et al., "Use of a Phosphorous-Enriched Dialysis Solution to Hemodialyze a Patient with Lithium Intoxication," Artificial Organs, vol. 19, No. 1, 1995, pp. 94-95.
Health Canada, Class Monograph, Haemodialysis Solutions, pp. 1-5 (Year: 1996).

DIALYSIS SOLUTION, FORMULATED AND STORED IN TWO PARTS, COMPRISING PHOSPHATE

This application is a continuation of U.S. application Ser. No. 15/057,219, filed Mar. 1, 2016, which is a divisional of U.S. application Ser. No. 11/658,001, filed Nov. 2, 2007, and which is a U.S. National Stage Application of International Application No. PCT/SE2005/01550 with an International Filing Date of Oct. 14, 2005 (published in English on Apr. 20, 2006 as International Patent Publication No. WO 2006/041409), which claims the benefit of U.S. Provisional Application No. 60/522,624, filed Oct. 21, 2004, and Swedish Application No. 0402507-8, filed Oct. 14, 2004, all of which are incorporated herein by reference in their entireties.

TECHNICAL FIELD

The present invention relates to a medical solution, a method for producing and use thereof. Particularly the present invention relates to a medical solution for dialysis.

BACKGROUND OF THE INVENTION

Dialysis is the indicated treatment for patients whose kidney function is failing. The removal of waste substances from the blood is effected by transfer to an external fluid or replacement of plasma liquid by an external fluid. Various dialysis techniques, with associated dialysis fluids, can be differentiated, which are used depending on the type of patient. In the case of patients suffering from long-term renal insufficiency, the dialysis technique used is usually an intermittent treatment of few times (2 to 3 times) per week for a few hours (3 to 5 hours). With this technique, known as hemodialysis, waste substances, in particular urea, salts and other small molecules, are removed from the blood by means of diffusion through a semi-permeable membrane. Another form of dialysis is peritoneal dialysis. In contrast to hemodialysis, where the blood is passed over a dialysis fluid in a dialysis unit (artificial kidney) outside the body, in the case of peritoneal dialysis a dialysis fluid is introduced into a patient's abdominal cavity (peritoneum), wherein the peritoneum is acting as a semi-permeable membrane.

In the case of patients suffering from acute renal insufficiency, a continuous treatment, throughout the entire day for several weeks, a continuous renal replacement therapy (CRRT), is the indicated treatment. A technique other than hemodialysis, specifically hemofiltration, is used for this. In the case of hemofiltration, waste substances are removed from the blood by means of convective flow through a highly permeable membrane. In this way the above-mentioned waste substances are removed in larger amounts and large(r) molecules are also removed. In addition, in the case of hemofiltration and appreciable quantity of liquid, which can vary from 1 to 5 liters per hour, is removed from the bloodstream. In contrast to hemodialysis, this demands that in the case of hemofiltration a replacement fluid must be returned to the patient in large quantities. Optionally a combination of dialysis and filtration can be used. This is called hemodiafiltration. A specific type of hemodiafiltration is continuous veno-venous hemodiafiltration, abbreviation as CVVHDF.

Under certain circumstances, in patients receiving regular thrice-weekly hemodialysis treatments and more frequently in patients undergoing CRRT Hypophosphatemia could occur. In the first case it is mainly due to an excessive ingestion of phosphate binders, inadequate administration of phosphate salts in parenteral nutrition and continued removal of phosphorus by dialysis. In the second case it is mainly a consequence of the efficient removal of phosphorus from patients having normal renal function from the beginning and thus a normal serum phosphorus level.

Hypophosphatemia is prevented and treated principally via the oral and the intravenous routes, for example by ingestion of phosphorus-rich foodstuffs, by oral phosphorus preparations or by intravenous administration of sodium (or potassium) phosphate salts. However the administration of phosphorus via oral and intravenous routes must be carried out with great caution, since it is impossible to determine the precise magnitude of the total phosphorus deficit, it is difficult to decide the correct amount of phosphorus to be administered to the patient. If too much phosphorus is administered hyperphosphatemia might develop, having serious consequences for the patient, for example hypocalcaemia, metastatic calcification and hypotensions, and if too little phosphorus is administered the hypophosphatemia is not corrected.

The use of solution containing both calcium ions and phosphate is used in solutions for total parenteral nutrition (TPN). The TPN solutions is packed in multi-compartment bags with lipids in a first compartment, amino acids and phosphate and most of the electrolytes except calcium in a second compartment, and a third compartment containing calcium and glucose. The main difference compared to a medical solution according to the invention is that the pH of the final, ready-for-use solutions is much lower than in the solutions showed in this invention, The TPN solutions normally have a pH between 5.2-6.

In U.S. Pat. No. 6,743,191 a substitution infusion fluid is disclosed, which infusion fluid comprises among other 0.2-1.0 mM dihydrogen phosphate ions, preferably 0.5-0.9 mM, and 1.6-2.6 mM calcium ions, preferably 1.9-2.4. The substitution infusion fluid according to this disclosure may conveniently be prepared by dissolving salts in water in such amounts that the desired concentrations are reached, as is well within the expertise of the normal person skilled in the art. During the preparation it is desired that a sterile environment be maintained.

In U.S. Pat. No. 6,017,942 an intravenous solution for treating patient with chronic renal failure is disclosed, which solution comprises among other approximate 0-20 mM phosphate and approximate 0-10 mM calcium. This solution is to be administered 1-3 times per day.

The problem when introducing phosphorus in a medical solution is the formation of various calcium phosphates that precipitate and the risk for precipitation is further increased if the fluid is exposed to terminal heat sterilization. The solubility of calcium phosphates depends on the concentrations of calcium and phosphate, respectively, and further on the presence of other electrolytes, temperature and pH. As long as the pH is about 5.2-6, as in the TPN solutions, there is no risk of precipitation, but in physiological solutions with pH values equal to physiological pH of about 7-7.6, the risk of precipitation is enhanced. Accordingly, it is not only the pH during sterilization and storage that need to be controlled, also the pH in a mixed and ready-for-use solution needs to be controlled. The problem is also that many of these fluids should be stable during long-term storage, up to two years.

In one of the above-identified references this is solved by having the composition for the solution as a powder up until use and then dissolve it in a fluid before administration. However, even if trying to maintain sterility according to the European pharmacopoeia to thereby avoid the risk of infection in a patient, this is not an optimal way to maintain sterility. If a package is brought in connection with the atmosphere by e.g. injecting a solution component into a bag with a solution, this solution is no longer a sterile solution. Instead it is an aseptic solution, and aseptic solutions as such are not allowed to be infused into a patient.

The best way would be to have the solution terminal sterilized in its packaging in order to make sure that the solution is as sterile as possible and to be kept in this sterile environment also during mixing into a ready-for-use solution without opening up the bag and expose the content therein for contamination.

SUMMARY OF THE INVENTION

One object of the invention is to provide a medical solution that ensures good stability, both during storage and during use, that contains no precipitates and is sterile.

The present invention relates to a medical solution. According to the invention the ready-for-use solution comprises phosphate in a concentration of 1.0-2.8 mM, is sterile and has a pH of 6.5-7.6.

In one embodiment of the invention, said medical solution, in it's state of ready-for-use solution, comprises phosphate in a concentration of 1.2-2.6 mM and has a pH of 6.5-7.6.

In another embodiment said medical solution, in it's state of ready-for-use solution, comprises phosphate in a concentration of up to about 2.8 mM and has a pH of 6.5-7.4.

In another embodiment said medical solution, in it's state of ready-for-use solution, comprises phosphate in a concentration of up to about 1.3 mM and has a pH of 6.5-7.6.

In a further embodiment the medical solution is divided into at least two single solutions before use, wherein a first single solution comprises at least one buffer chosen from the group comprising acetate, lactate, citrate, pyruvate, carbonate and bicarbonate and a second single solution comprises an acid, wherein said first and second single solutions, after terminal sterilization and up on use, are to be mixed to form a ready-for-use solution, and wherein said ready-for-use solution has a pH of 6.5-7.6.

In another embodiment said second single solution has a pH below 2.5.

In another embodiment said first single solution comprises bicarbonate and carbonate in such proportions that the partial pressure of carbon dioxide, $CO_2$, in said first single solution is of the same order of magnitude as the partial pressure of carbon dioxide, $CO_2$, of the atmosphere, and said second single solution has a pH of 1.0-1.5, and said ready-for-use solution has a pH of 7.0-7.6.

In even an additional embodiment said first single solution has a pH of 10.1-10.5, preferably 10.3.

In another embodiment said second single solution has a pH of 1.3.

In another embodiment said second single solution comprises HCl.

In another embodiment said first single solution comprises the phosphate ions.

In another embodiment said second single solution comprises the phosphate ions.

In a further embodiment said ready-for-use solution further comprises one or more electrolytes, wherein said one or more electrolytes comprise one or more of the ions of sodium, calcium, potassium, magnesium and/or chloride. Said one or more electrolytes is/are before being mixed into the ready-for-use solution, arranged in said second single solution. In one embodiment sodium ions and/or chloride ions are, before being mixed into the ready-for-use solution, arranged both in said first and said second single solution.

In a further embodiment said first single solution comprises bicarbonate and phosphate, and said second single solution comprises calcium and/or magnesium.

In even a further embodiment said first single solution comprises lactate and phosphate, and said second single solution comprises calcium and/or magnesium.

In another embodiment said second single solution further comprises glucose.

The present invention further relates to a method for producing a medical solution. According to the invention, said method comprises providing said single solutions in separate compartments, and thereafter terminal sterilizing said single solutions.

The present invention further relates to a multi-compartment bag comprising the medical solution according to the invention.

Further the present invention relates to the use of a medical solution according to the invention.

Additional objects, features, advantages and preferred embodiments of the present invention will become apparent from the following detailed description when taken in conjunction with the enclosed patent claims.

Definitions

The term "medical solution" is intended to mean dialysis solutions for hemodialysis, hemodiafiltration, hemofiltration, and peritoneal dialysis, solutions for dialysis within renal intensive care, solutions for substitution or infusion normally containing buffering substances, and solutions for nutrition purposes.

The term "single solution" is intended to mean one solution kept isolated from other solutions up until use.

The term "bicarbonate and carbonate" is intended to mean alkali bicarbonate and alkali carbonate, especially sodium bicarbonate and sodium carbonate.

The term "a ready-for-use solution" is intended to mean a solution which includes the required different single solutions and which is ready for use.

The term "multi-compartment bag" is intended to mean a bag divided into more than one compartment and that the content in the different compartments could be brought together and mixed before use.

The term "terminal sterilization" is intended to mean that the product is sterilized in its final package. The terminal sterilization may include heat sterilization and/or radiation sterilization, but is preferably heat sterilization effected in an autoclave at a temperature of at least 100° C., preferably at least 121° C.

The term "up on use" is intended to mean as close as possible before the medical solution is used for it's specific purpose.

The term "glucose or glucose-like compounds" is intended to mean glucose, polymers of glucose such as cellulose and starch as well as other molecules containing at least on glucose unit i.e. disaccharides, trisaccharides and polysaccharides (glycans).

DETAILED DESCRIPTION OF THE INVENTION

The inventors of the present invention have found that during specific circumstances, concentrations, pH ranges and packaging, a sterile, stabile phosphate containing medical solution could be provided, and it is this which constitute the base for the present invention.

One of the more important matters searching for the most favorable circumstances, concentrations, pH ranges and packaging is the formation of particles during production, storage and preparation for a ready-for-use solution. The amount of particles has to stay in between specific ranges both concerning the size of the particles as well as the amount of particles. This is specified within the European Pharmacopoeia, and for particles in the size of 10 µm the limit is 25 counts/ml. It is very important that the particle formation is kept to a minimum, otherwise the immune system could get triggered, which could lead to start of the inflammatory cascade. A further problem with the presence of particle is the risk of clogging the filters, which are used during the dialysis treatment.

The main components that give rise to the problem of particle formation are calcium ions in combination with either carbonate and/or phosphate.

The first instant thought to solve the problem is of course to keep calcium ions separated from carbonate and phosphate during production and storage, but the problem is still there when preparing the ready-for-use solution, whereby the formation of solid calcium carbonate and calcium phosphate still could be formed during mixing.

The present inventors have found that, with a phosphate concentration of up to about 2.8 mM in the ready-for-use solution, the amount of formed particles are within the allowed limits if the pH value in the ready-for-use solution is kept to at most 7.4, preferably at most 7.2.

If the phosphate concentration is up to about 1.3 mM in the ready-for-use solution an allowed amount of particles are formed if the pH value in the ready-for-use solution is kept to at most 7.6, preferably at most 7.4.

The present inventors have also found that calcium and phosphate could be kept together during preparation and storage if these two components are kept in a compartment with a pH below 2.5, preferably below 1.5, and most preferably below or equal to 1.3.

In one embodiment of the invention the medical solution is before use divided into at least two single solutions, a first single solution and a second single, wherein said first and second single solutions, after terminal sterilization and up on use, are to be mixed to form a final solution with a pH of 6.5-7.6.

Said first single solution comprises at least one buffer chosen from the group comprising acetate, lactate, citrate, pyruvate, carbonate and bicarbonate and said second single solution comprises an acid.

In another embodiment of the invention said first single solution comprises bicarbonate and carbonate in such proportions that the partial pressure of carbon dioxide, $CO_2$, in the first single solution is of the same order of magnitude as the partial pressure of carbon dioxide, $CO_2$, of the atmosphere. Bicarbonate and carbonate are preferably mixed as sodium bicarbonate and sodium carbonate, and in one embodiment said first single solution has a pH within the range of 10.1-10.5, preferably 10.3.

By adjusting the partial pressure of carbon dioxide, $CO_2$, in the first single solution in the same order of magnitude as the partial pressure of carbon dioxide, $CO_2$, in the atmosphere, the carbon dioxide in the compartment for the first single solution stays within the bag compartment and does not enter out of the bag material out into the atmosphere, as the partial pressure of $CO_2$ within the liquid is in equilibrium with the partial pressure of $CO_2$ in the atmosphere.

After having mixed said first and second single solutions in this embodiment into a ready-for-use solution, said ready-for-use solution has a pH within the range of 7.0-7.6. Further, said ready-for-use solution preferably has a bicarbonate concentration of at least 25 mM, preferably at least 30 mM, and at most 45 mM, preferably at most 40 mM.

However, the combination of bicarbonate/carbonate in said first single solution could in another embodiment, as stated above, be exchanged to or supplemented by one or more of the buffers chosen from the group comprising acetate, lactate, citrate and pyruvate. In one embodiment, the buffer is bicarbonate in a concentration of 25-35 mM with optionally 0-15 mM lactate added, wherein the concentration given is the concentration in the ready-for-use solution.

In one embodiment said second single solution preferably has a pH within the range of 1.0-1.5, most preferably a pH of 1.3. In one embodiment of the invention said second single solution comprises HCl.

In one embodiment said ready-for-use solution further comprises one or more electrolytes. The electrolytes are one or more of the ions of sodium, calcium, potassium, magnesium and/or chloride. The arrangement of the electrolytes in the different compartments is dependent on the different electrolytes co-behavior with the other substances present in said single solutions, i.e. whether some sort of reaction could occur between one or more of the electrolyte(s) and the other substances present in a specific single solution. Usually, the electrolytes are contained in said second single solution. For example, calcium ions and magnesium ions are preferably provided in any of the other single solutions, but said first single solution when said first single solution comprise the combination of bicarbonate/carbonate, only bicarbonate and/or phosphate. The reason for this is that calcium and magnesium and bicarbonate/carbonate, bicarbonate and/or phosphate together could cause precipitation of calcium carbonate, magnesium carbonate, calcium phosphate and magnesium phosphate. However, calcium ions and magnesium ions could be kept with bicarbonate under certain circumstances, such as specific pH ranges and so on, this is for example disclosed in EP 0 437 274, which hereby is enclosed by reference. Further calcium and magnesium could be kept with phosphate also under certain circumstances, see above of this.

Sodium ions and/or chloride ions, on the other hand, are usually arranged in both said first and said second single solutions.

Said medical solution could further comprise glucose or glucose-like compounds, and in one embodiment the glucose or glucose-like compounds is arranged in said second single solution. During sterilization and storage glucose or glucose-like compounds should be kept at a low pH value in order to ensure that the formation of glucose degradation products (GDPs) are kept to a minimum. In one embodiment the pH in the second single solution is below 2.5.

In the method for producing a medical solution according to above, said single solutions are provided in separate compartments. Thereafter said single solutions are terminally sterilized. Preferably, the terminal sterilization is heat sterilization and/or radiation sterilization, (see also European Pharmacopoeia 1977 for a review of different sterilization techniques). In one embodiment of the method according to the invention, the terminal sterilization is heat sterilization at a temperature of at least 100° C., preferably at least 121° C.

The sterilization time may vary depending on the sterilization temperature, the type of container and the contents therein to be sterilized.

The radiation sterilization may be either ionising or non-ionising sterilization. Examples of ionising sterilization are gamma and beta radiation. Examples of non-ionising radiation sterilization is UV radiation.

The medical solution according to the present invention has the advantage of ensuring good stability and good biocompatibility.

Said single solutions could be provided in different compartments in a multi-compartment bag, and the mixing could be provided by having the different compartments coupled by frangible pins, which pins could be broken in order to mix the content in the different compartments within the multi-compartment bag. The mixing could further be provided by having a peal seal in-between the different compartments, which peal seals could be pealed in order to mix the content in the different compartments.

EXAMPLES

Below you will find different examples of solutions according to the present invention.

Example 1

The following pairs of single solutions were prepared according to the table 1-5 below. The volume relationship between the first single solutions and the second single solutions are 1:20.

TABLE 1

(solution 1)

|  | First single solution (basic part) (mM) | Second single solution (acid part) (mM) |
|---|---|---|
| $Na^+$ | 1461.0 | 70.5 |
| $Cl^-$ | — | 113.6* |
| $Ca^{2+}$ | — | 1.8 |
| $Mg^{2+}$ | — | 0.5 |
| $HCO_3^-$ | 139.0 | — |
| $CO_3^{2-}$ | 661.0 | — |
| $H_2PO_4^-$ | — | — |

*Chloride ions have been added as NaCl, CaCl$_2$, MgCl$_2$, and HCl.

TABLE 2

(solution 2)

|  | First single solution (basic part) (mM) | Second single solution (acid part) (mM) |
|---|---|---|
| $Na^+$ | 1487.0 | 70.5 |
| $Cl^-$ | — | 113.6* |
| $Ca^{2+}$ | — | 1.8 |
| $Mg^{2+}$ | — | 0.5 |
| $HCO_3^-$ | 139.0 | — |
| $CO_3^{2-}$ | 661.0 | — |
| $H_2PO_4^-$ | 26 | — |

*Chloride ions have been added as NaCl, CaCl$_2$, MgCl$_2$, and HCl.

TABLE 3

(solution 3)

|  | First single solution (basic part) (mM) | Second single solution (acid part) (mM) |
|---|---|---|
| $Na^+$ | 1513.0 | 70.5 |
| $Cl^-$ | — | 113.6* |
| $Ca^{2+}$ | — | 1.8 |
| $Mg^{2+}$ | — | 0.5 |
| $HCO_3^-$ | 139.0 | — |
| $CO_3^{2-}$ | 661.0 | — |
| $H_2PO_4^-$ | 52 | — |

*Chloride ions have been added as NaCl, CaCl$_2$, MgCl$_2$, and HCl.

TABLE 4

(solution 4)

|  | First single solution (basic part) (mM) | Second single solution (acid part) (mM) |
|---|---|---|
| $Na^+$ | 1461.0 | 71.8 |
| $Cl^-$ | — | 113.6* |
| $Ca^{2+}$ | — | 1.8 |
| $Mg^{2+}$ | — | 0.5 |
| $HCO_3^-$ | 139.0 | — |
| $CO_3^{2-}$ | 661.0 | — |
| $H_2PO_4^-$ | — | 1.3 |

*Chloride ions have been added as NaCl, CaCl$_2$, MgCl$_2$, and HCl.

TABLE 5

(solution 5)

|  | First single solution (basic part) (mM) | Second single solution (acid part) (mM) |
|---|---|---|
| $Na^+$ | 1461.0 | 73.1 |
| $Cl^-$ | — | 113.6* |
| $Ca^{2+}$ | — | 1.8 |
| $Mg^{2+}$ | — | 0.5 |
| $HCO_3^-$ | 139.0 | — |
| $CO_3^{2-}$ | 661.0 | — |
| $H_2PO_4^-$ | — | 2.6 |

*Chloride ions have been added as NaCl, CaCl$_2$, MgCl$_2$, and HCl.

The solutions were sterilized in an autoclave at 121° C. for 40 minutes. After sterilization, the first and second solution in each pair were mixed and the amounts of particles in the sizes 2, 5 and 10 μm, respectively, were measured. The results are presented in table 6 below.

TABLE 6

| | Mixed ready-for-use solution (mM) | | | | | | | Particles counts/ml | | |
|---|---|---|---|---|---|---|---|---|---|---|
| | $Na^+$ | $Cl^-$ | $Ca^{2+}$ | $Mg^{2+}$ | $HCO_3^-$ | $CO_3^{2-}$ | $H_2PO_4^-$ | 2 μm | 5 μm | 10 μm |
| Solution 1 | 143.6 | 108.0 | 1.7 | 0.5 | 6.9 | 33.0 | — | 140 | 59 | 13 |
| Solution 2 | 144.8 | 108.0 | 1.7 | 0.5 | 6.9 | 33.0 | 1.3 | 75 | 30 | 5 |
| Solution 3 | 146.2 | 108.0 | 1.7 | 0.5 | 6.9 | 33.0 | 2.6 | 75 | 29 | 5 |
| Solution 4 | 144.8 | 108.0 | 1.7 | 0.5 | 6.9 | 33.0 | 1.2 | 194 | 84 | 16 |
| Solution 5 | 146.2 | 108.0 | 1.7 | 0.5 | 6.9 | 33.0 | 2.5 | 199 | 72 | 11 |

The particle counts were made by with the help of a HIAC Model 9703 Liquid Particle Counting System (serie No. F08504) with the software version Pharm, Spec. 1,4.

As evident from the results above in table 6, the resulting ready-for-use solutions according to the invention is well under the limits given in the European Pharmacopoeia.

Example 2

In order to find out the optimal pH ranges for the ready-for-use solution in order to keep the formation of particles to a minimum the following pair of single solutions according to table 7 was prepared and mixed. The volume relation between the first single solution and the second single solution is 1:20.

TABLE 7

| | First single solution (basic part) (mM) | Second single solution (acid part) (mM) | Mixed ready-for-use solution (mM) |
|---|---|---|---|
| $Na^+$ | 1461.0 | 70.5 | 143.6 |
| $Cl^-$ | — | 113.6* | 108.0 |
| $Ca^{2+}$ | — | 1.8 | 1.7 |
| $Mg^{2+}$ | — | 0.5 | 0.5 |
| $HCO_3^-$ | 139.0 | — | 6.9 |
| $CO_3^{2-}$ | 661.0 | — | 33.0 |

*Chloride ions have been added as NaCl, $CaCl_2$, $MgCl_2$, and HCl.

The mixed solution was split in two parts, and 1.3 mM $NaH_2PO_4$ were added to one part and 2.6 mM $NaH_2PO_4$ were added to the other part. The two different solutions were pooled in 50 ml glass bottles and in each group of bottles with the two different concentrations of $NaH_2PO_4$ the pH was adjusted to 6.8, 7.0, 7.2, 7.4, 7.6, 7.8, 8.0, and 8.2. The amount of particles was measured 24 hours later.

Figure 1A:
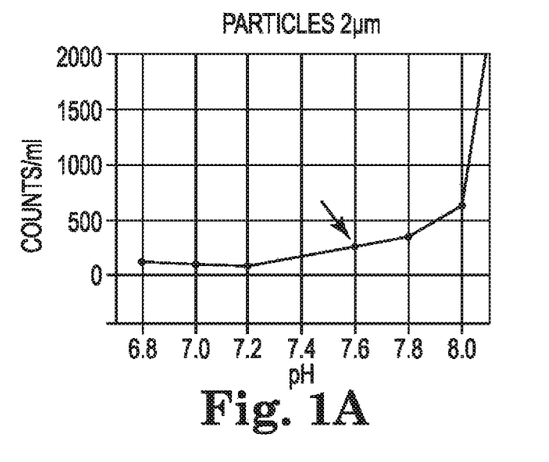
FIGS. 1A-C are graphs showing the relationship between pH value in the final ready-for-use solution and the amount produced particles 24 hours after mixing for a solution containing 1.3 mM phosphate.
Figure 1B:
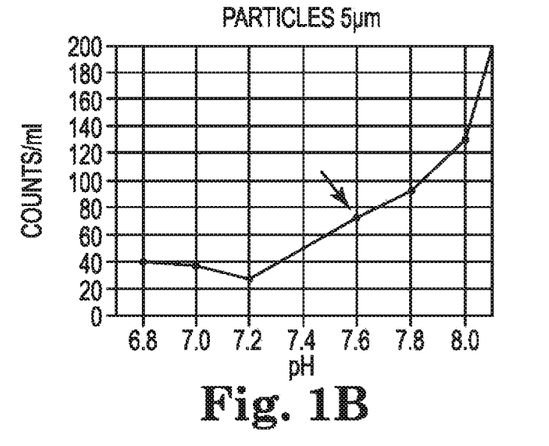
Figure 1C:
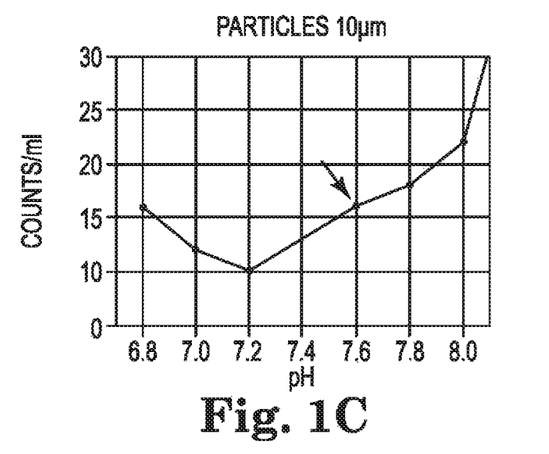
Figure 2A:
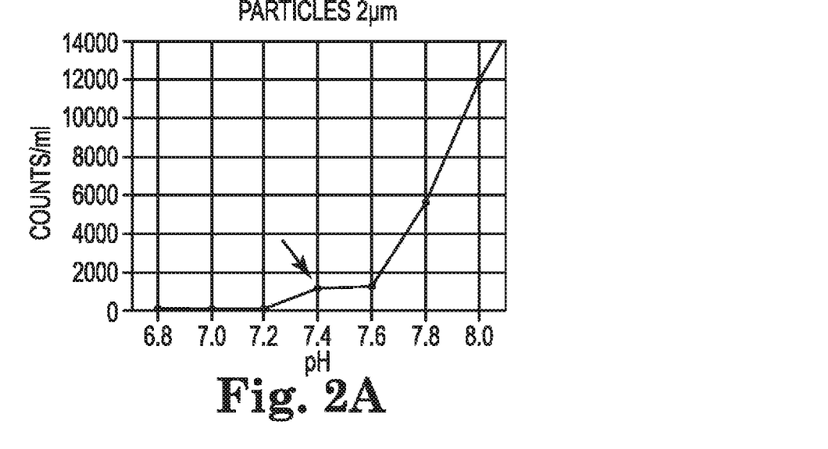
FIGS. 2A-C are graphs showing the relationship between pH value in the final ready-for-use solution and the amount produced particles 24 hours after mixing for a solution containing 2.6 mM phosphate.
Figure 2B:
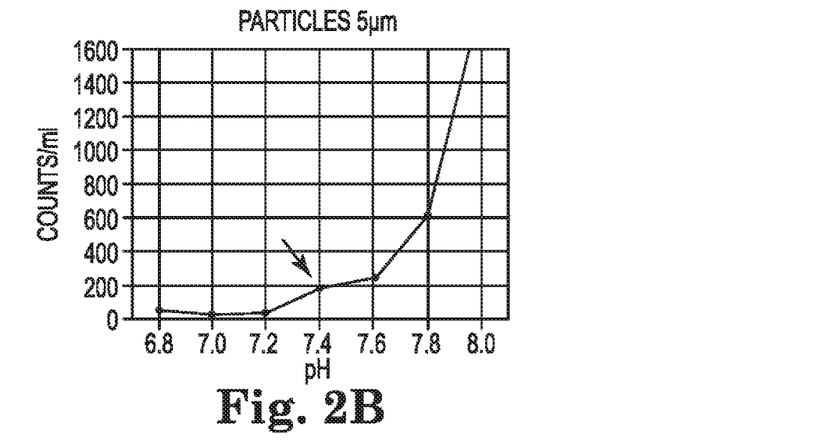
Figure 2C:
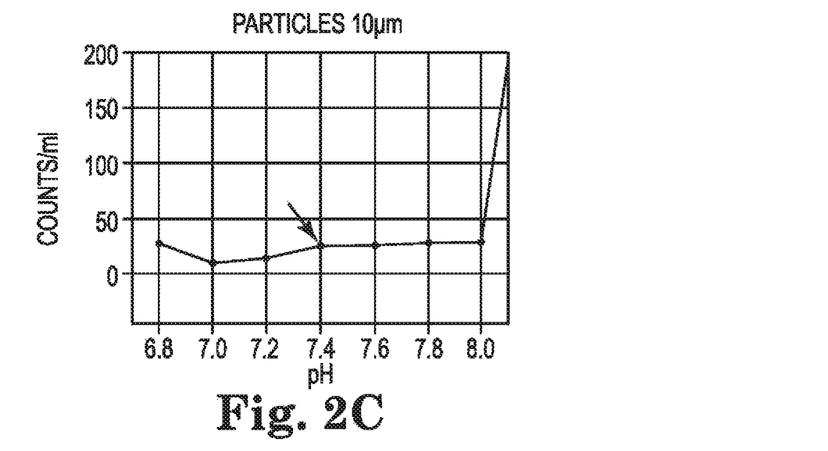

In the enclosed FIGS. 1A-1C the results from this measurements are seen for the solution containing 1.3 mM phosphate. In the enclosed FIGS. 2A-2B the results form this measurements are seen for the solution containing 2.6 mM phosphate.

As evident from the figures, the pH in a ready-for-use solution with a phosphate concentration of 1.3 mM should be below or equal to 7.6, preferably below or equal to 7.4. In a ready-for-use solution with a phosphate concentration of 2.6 mM the pH should be below or equal to 7.4, preferably below or equal to 7.2. Particle formation is normally first observed in the very small size and than they aggregate and form larger particles. The chosen pH upper limits of 7.4 and 7.6, respectively, is based on changes in the particle profile rather than on absolute values. All measured particle sizes where included in the evaluation with some extra focus on the small particles preceding the formation of larger particles.

Example 3

In order to find out the optimal upper limit for the phosphate concentration for the ready-for-use solution in order to keep the formation of particles to a minimum, the following pair of single solutions according to table 8 was prepared. The volume relationship between the first and the second single solution was 1:20.

TABLE 8

| | First single solution (basic part) (mM) | Second single solution (acid part) (mM) | Mixed ready-for-use solution (mM) |
|---|---|---|---|
| $Na^+$ | 1461.0 | 70.5 | 143.6 |
| $Cl^-$ | — | 113.6* | 108.0 |
| $Ca^{2+}$ | — | 1.8 | 1.7 |
| $Mg^{2+}$ | — | 0.5 | 0.5 |
| $HCO_3^-$ | 139.0 | — | 6.9 |
| $CO_3^{2-}$ | 661.0 | — | 33.0 |

*Chloride ions have been added as NaCl, $CaCl_2$, $MgCl_2$, and HCl.

The first and second single solutions were mixed and split in 5 different parts and phosphate was added in the following concentrations 2.6, 2.8, 3.0, 3.5 and 4.0. pH was adjusted to 7.6 and the amount of particles was measured at 0 hour and 24 hours after mixing.

Figure 3A:
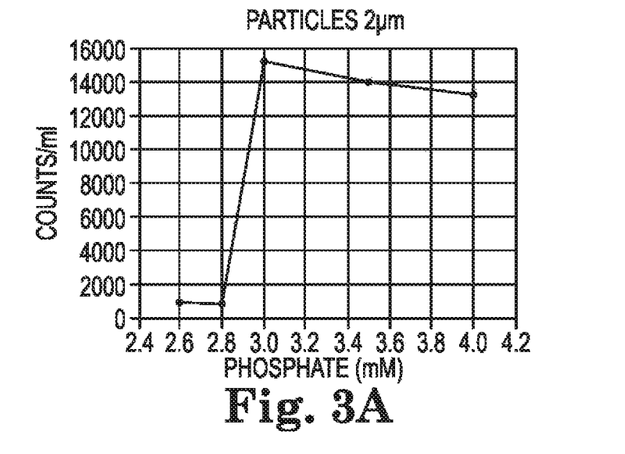
FIGS. 3A-C are graphs showing the relationship between phosphate concentration and the amount of produced particles 24 hours after mixing for a solution having a pH of 7.6.
Figure 3B:
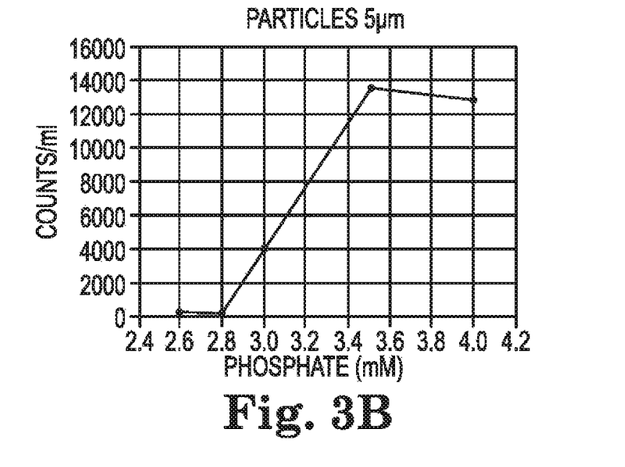
Figure 3C:
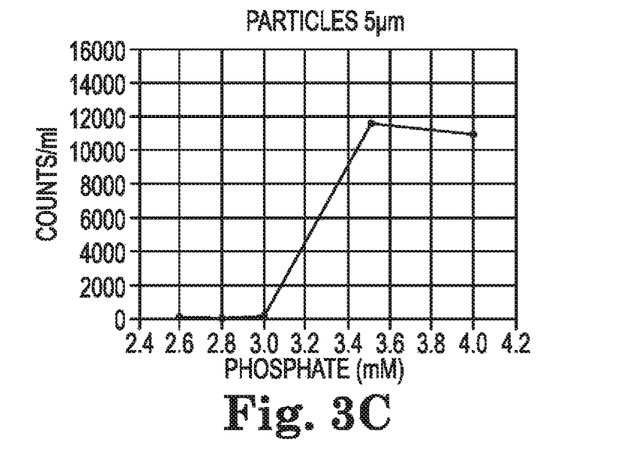

The results are shown in FIGS. 3A-C, and from the figures it could be concluded that the solution is stable during 24 hours at a phosphate concentration less or equal to 2.8 mM phosphate and a pH of 7.6.

Accordingly, by having a phosphate concentration of 1.0-2.8 in a final ready-for-use solution with a pH of 6.5-7.6 a sterile, stable phosphate containing medical solution could be provided.

Example 4

The following pairs of single solutions were prepared according to the tables 9-11 and constitute different embodiments of the present invention. The volume relationship between the first single solution and the second single solution in these pairs of solutions are 20:1. Accordingly, this time the second single solution has the small volume and the first single solution has the larger volume.

TABLE 9

| | First single solution (basic part) (mM) | Second single solution (acid part) (mM) | Mixed ready-for-use solution (mM) |
|---|---|---|---|
| $Na^{+1)}$ | 147.3 | | 140.0 |
| $Ca^{2+}$ | | 25.0 | 1.25 |
| $Mg^{2+}$ | | 12.0 | 0.6 |
| $K^+$ | 4.21 | | 4.0 |
| $Cl^{-\ 2)}$ | 114.3 | 74.0 | 115.9 |
| $HCO_3^-$ | 34.74 [4)] | | 30.0 |
| Lactate | | | 0 |
| $HPO_4^{2-\ 3)}$ | 1.26 | | 1.20 |
| Glucose | | 100.0 | 5.00 |
| HCl | | 72.0 | |
| pH | 7.7-8.2 | 1.3-1.6 | 7.0-7.6 |

[1)] Sodium is added as NaCl, NaHCO₃, and Na₂HPO₄.
[2)] Chloride is added as NaCl, KCl, CaCl₂, MgCl₂ and HCl.
[3)] Phosphate is added as Na₂HPO₄, but after mixing the two single solutions it will be present mainly as $HPO_4^{2-}$. However, $H_2PO_4^-$ and $PO_3^{3-}$ will also be present due to the equilibrium between these ions. The concentration of each ion will depend on the pH.
[4)] The amount of bicarbonate is overdosed, since some bicarbonate will convert to $CO_2$ during mixing and thus leave the solution.

TABLE 10

| | First single solution (basic part) (mM) | Second single solution (acid part) (mM) | Mixed ready-for-use solution (mM) |
|---|---|---|---|
| $Na^{+1)}$ | 147.4 | | 140.0 |
| $Ca^{2+}$ | | 30.0 | 1.5 |
| $Mg^{2+}$ | | 10.0 | 0.5 |
| $K^+$ | | | 0 |
| $Cl^{-\ 2)}$ | 104.8 | 80.0 | 107.2 |
| $HCO_3^-$ | 40.0 [4)] | | 35.0 |
| Lactate | | | 0 |
| $HPO_4^{2-\ 3)}$ | 1.26 | | 1.2 |
| Glucose | | | 0 |
| HCl | | 72.0 | |
| pH | 7.7-8.3 | 1.3-1.6 | 7.0-7.6 |

[1)] Sodium is added as NaCl, NaHCO₃, Na₂HPO₄ and sodium lactate.
[2)] Chloride is added as NaCl, CaCl₂, MgCl₂ and HO.
[3)] Phosphate is added as Na₂HPO₄, but after mixing the two single solutions it will be present mainly as $HPO_4^{2-}$. However, $H_2PO_4^-$ and $PO_3^{3-}$ will also be present due to the equilibrium between these ions. The concentration of each ion will depend on the pH.
[4)] The amount of bicarbonate is overdosed, since some bicarbonate will convert to $CO_2$ during mixing and thus leave the solution.

TABLE 11

| | First single solution (basic part) (mM) | Second single solution (acid part) (mM) | Mixed ready-for-use solution (mM) |
|---|---|---|---|
| $Na^{+1)}$ | 147.4 | | 140.0 |
| $Ca^{2+}$ | | 25.0 | 1.25 |
| $Mg^{2+}$ | | 12.0 | 0.6 |
| $K^+$ | 4.2 | | 4.0 |
| $Cl^{-\ 2)}$ | 149.1 | 74-0 | 145.9 |
| $HCO_3^-$ | | | 0 |
| Lactate | 36.8 | | 35.0 |
| $HPO_4^{2-\ 3)}$ | 1.26 | | 1.2 |
| Glucose | | 100.0 | 5.0 |
| HCl | | 12.0 | |
| pH | 7-4-7.9 | 1.9-2.2 | 6.5-7.0 |

[1)] Sodium is added as NaCl,, Na₂HPO₄ and sodium lactate.
[2)] Chloride is added as NaCl, CaCl₂, MgCl₂ and HCl.
[3)] Phosphate is added as Na₂HPO₄, but after mixing the two single solutions it will be present mainly as $HPO_4^{2-}$. However, $H_2PO_4^-$ and $PO_3^{3-}$ will also be present due to the equilibrium between these ions. The concentration of each ion will depend on the pH.

Example 5

The following pair of single solutions was prepared according to the table 12 and constitutes an embodiment of the present invention. The volume relationship between the first single solution and the second single solution in this pair is 1:20.

TABLE 12

| | First single solution (basic part) (mM) | Second single solution (acid part) (mM) | Mixed ready-for-use solution (mM) |
|---|---|---|---|
| $Na^{+1)}$ | 1256 | 81.25 | 140 |
| $Ca^{2+}$ | | 1.32 | 1.25 |
| $Mg^{2+}$ | | 0.63 | 0.6 |
| $K^+$ | | 4.21 | 4 |
| $Cl^{-\ 2)}$ | | 121 | 114.9 |
| $HCO_3^-$ | 132 | | 6.6 |
| $CO_3^{2-}$ | 538 | | 26.9 |
| $HPO_4^{2-\ 3)}$ | 24 | | 1.2 |
| Glucose | | 5.26 | 5.00 (0.9 g/l) |
| HCl | | 31.6 | |
| pH | 10.3 | 1.5 | 7.25 |

[1)] Sodium is added as NaCl, NaHCO₃, Na₂CO₃, and Na₂HPO₄.
[2)] Chloride is added as NaCl, KCl, CaCl₂, MgCl₂ and HCl.
[3)] Phosphate is added as Na₂HPO₄, but after mixing the two single solutions it will be present mainly as $HPO_4^{2-}$. However, $H_2PO_4^-$ and $PO_3^{3-}$ will also be present due to the equilibrium between these ions. The concentration of each ion will depend on the pH.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

The invention claimed is:

1. A ready-for-use dialysis solution obtained by mixing a first single solution with a second single solution,
    wherein said first single solution comprises phosphate ions and at least one buffer chosen from the group comprising bicarbonate and lactate and wherein said first single solution has a pH of 7.4-8.3;
    wherein said second single solution comprises calcium, magnesium and HCl and has a pH of 1.3-2.2;
    wherein said mixing of said first and second single solutions is performed after terminal sterilization and upon use to form the ready-for-use dialysis solution;
    wherein the ready-for-use dialysis solution comprises phosphate in a concentration of 1.2-2.6 mM, calcium, magnesium, and chloride;
    wherein said ready-to-use dialysis solution is sterile and has a pH of 6.5-7.6;
    wherein the ready-for use dialysis solution is a hemodialysis solution, a hemofiltration solution, or a hemodiafiltration solution; and
    wherein within 24 hours of mixing the ready-for-use dialysis solution is stable and particles of 10 μm are less than 25 counts/ml.

2. A ready-for-use dialysis solution according to claim 1, wherein said first single solution further comprises potassium.

3. A ready-for-use dialysis solution according to claim 1, wherein said second single solution further comprises glucose or glucose-like compounds.

4. A method for producing a ready-for-use dialysis solution according to claim 1, said method comprising the steps of:
    providing said first and second single solutions in separate compartments, and terminally sterilizing said first and second single solutions.

5. A ready-for-use dialysis solution according to claim 1, wherein the pH of the ready-for-use dialysis solution is 6.5-7.0 or 7.0-7.6.

6. A ready-for-use dialysis solution obtained by mixing a first single solution with a second single solution,
- wherein said first single solution comprises phosphate ions, carbonate, and bicarbonate;
- wherein said second single solution comprises calcium, magnesium and HCl and has a pH of 1.0-1.5;
- wherein said mixing of said first and second single solutions is performed after terminal sterilization and upon use to form the ready-for-use dialysis solution;
- wherein the ready-for-use dialysis solution comprises phosphate at a concentration of 1.3-2.6 mM, carbonate, bicarbonate, calcium, magnesium, and chloride;
- wherein said ready-to-use dialysis solution is sterile and has a pH of 7.0-7.6;
- wherein the ready-for use dialysis solution is a hemodialysis solution, a hemofiltration solution, or a hemodiafiltration solution; and
- wherein within 24 hours of mixing the ready-for-use dialysis solution is stable and particles of 10 μm are less than 25 counts/ml.

7. A ready-for-use dialysis solution according to claim 6, wherein said second single solution has a pH of 1.3.

8. A ready-for-use dialysis solution according to claim 6, wherein said first single solution further comprises potassium.

9. A ready-for-use dialysis solution according to claim 6, wherein said second single solution further comprises glucose or glucose-like compounds.

10. A method for producing a ready-for-use dialysis solution according to claim 6 said method comprising the steps of:
- providing said first and second single solutions in separate compartments, and
- terminally sterilizing said first and second single solutions.

* * * * *